United States Patent [19]

Harrel

[11] Patent Number: 5,122,153
[45] Date of Patent: Jun. 16, 1992

[54] TISSUE REMOVING INSTRUMENT AND METHOD

[76] Inventor: Stephen K. Harrel, 4510 Ridge Rd., Dallas, Tex. 75229

[21] Appl. No.: 497,444

[22] Filed: Mar. 22, 1990

[51] Int. Cl.⁵ .............................................. A61B 17/32
[52] U.S. Cl. ..................................... 606/180; 433/91; 433/114; 604/22; 604/318
[58] Field of Search ............... 433/91, 114, 115, 116, 433/125; 606/180; 604/22, 318, 319

[56] References Cited

U.S. PATENT DOCUMENTS

| | | | |
|---|---|---|---|
| 2,655,725 | 10/1953 | Fehrman | 433/116 |
| 2,671,269 | 3/1954 | Francis | 433/116 |
| 2,703,904 | 3/1955 | De Long | 433/91 |
| 2,731,722 | 1/1956 | Wilen | 433/116 |
| 3,526,219 | 9/1970 | Balamuth | 433/91 |
| 3,542,372 | 11/1970 | Edwardson | 433/116 |
| 3,747,216 | 7/1973 | Bassi et al. | 433/91 |
| 3,786,566 | 1/1974 | Jelicic et al. | 433/116 |
| 4,061,146 | 12/1977 | Baehr et al. | 604/22 |
| 4,111,208 | 9/1978 | Leuenberger | 606/180 |
| 4,176,453 | 12/1979 | Abbott | 433/91 |
| 4,500,296 | 2/1985 | Friedman | 433/225 |
| 4,609,352 | 9/1986 | Riitano | 433/165 |
| 4,649,919 | 3/1987 | Thimsen et al. | 604/22 |
| 4,666,406 | 5/1987 | Kanca, III | 433/229 |
| 4,722,685 | 2/1988 | de Estrada | 433/116 |
| 4,764,114 | 8/1988 | Jeffcoat et al. | 433/72 |
| 4,917,603 | 4/1990 | Haack | 433/84 |

Primary Examiner—John J. Wilson
Attorney, Agent, or Firm—Richards, Medlock & Andrews

[57] ABSTRACT

A rotating bur is disposed in a small-diameter tissue removing suction tube to grind tissue drawn into an entrance end of the tube. The bur includes a grinding head recessed from the entrance end, and is closely spaced between the internal sidewalls of the suction tube to grind tissue entrained into the tube. The entrance end of the suction tube includes an annular sharp edge to facilitate removal of tissue strands from a tissue mass. The ground tissue is then conducted through the suction tube by the suction, and discharged into a remotely located container.

29 Claims, 1 Drawing Sheet

TISSUE REMOVING INSTRUMENT AND METHOD

TECHNICAL FIELD OF THE INVENTION

The present invention relates in general to medical and dental instruments, and more particularly relates to an instrument for selectively removing or disconnecting small pieces of tissue, reducing the tissue to smaller bits, and delivering the tissue bits to a remote collection unit.

BACKGROUND OF THE INVENTION

The medical and dental practice often require that both hard and soft tissue be removed in the treatment of a patient. The removal of damaged tissue or scar tissue is often necessary in order to prevent further deterioration of an organ. For example, in the treatment of periodontal diseases, such as pyorrhea, the removal of granulated tissue is necessary in order to arrest further deterioration of both the hard and soft tissues.

The current practice in removing the granulation or scar tissue adjacent a tooth is with the use of a curette. By continually scraping the granulation tissue with the curette, the sinewy tissue fibers are disconnected and removed. Generally, the tissue is scraped by a curette and then suctioned by other equipment to remove the tissue fragments. In some instances, the suction instrument and the curette scraping operation is conducted simultaneously.

The removal of the granulation tissue by a curette is a time-consuming and tedious process, often taking 5-8 minutes per tooth. Depending upon the number of teeth which are afflicted, it can be appreciated that the entire process can be stressful, both for the patient as well as the surgeon.

Especially adapted for use in the endodontic area is an instrument having a boring bit which can bore into the root of a tooth, and which includes a fluid tube capable of concurrent spraying the tooth and suctioning excess fluids. Such an instrument is disclosed in U.S. Pat. No. 3,747,216. However, the boring bit of such instrument protrudes substantially therefrom and is thus not well adapted for the selective removal of soft tissue.

On other occasions, both healthy and damaged tissue are required to be removed during other types of medical operations. Attendant with many such operations is the flow of body fluids which can obscure and frustrate the removal of tissue. In such cases, a suction device is employed at the same time as the instrument for removing tissue so that the surgeon can observe the area of interest. Again, the use of multiple instruments in the area of the operation, especially if the area is small, is counterproductive.

In both the medical and dental areas of practice, the tissue to be removed is often in a small or very inaccessible location. This is especially true in periodontic operations where the granulation tissue is recessed far below the gingival line, near the root of the tooth. In this instance, it becomes extremely difficult to cut the granulation tissue and remove it.

From the foregoing, it can be seen that a need exists for an instrument which can cut tissue and remove it in a more expedient manner than heretofore known. A further need exists for a tissue removing instrument which is effective to cut and remove tissue in narrow or tight places. Yet another need exists for a tissue removing instrument which grinds or cuts the tissue in extremely small bits, and removes the tissue bits, via suction, to a remote collection unit.

SUMMARY OF THE INVENTION

In accordance with the present invention, the disclosed tissue removing instrument, and corresponding methods, substantially reduce or eliminate the disadvantages and shortcomings associated with the prior art devices. According to the invention, a rotary driven grinding bur is disposed at the entrance end of a suction tube to grind tissue forced or drawn into the end of the suction tube. The entrance edge of the suction tube is preferably sharpened to facilitate the removal of pieces of tissue from a larger tissue mass.

In the preferred embodiment of the invention, the entrance annular edge of the suction tube is sharpened to facilitate cutting and separating the tissue. At a remote end of the tube there is connected a vacuum or suction to draw loose tissue bits and pieces through the tube. Between the entrance end and the vacuum end of the suction tube, there is disposed the rotating bur which functions to grind the tissue into smaller bits so that such bits can be carried away by the suction to a remote collection container. The rotating bur is preferably held in the chuck of a hand-held power-driven tool. The suction tube is held in a molded saddle member which is removably mounted to the head of the tool in such a manner that the grinding bur is radially centered within the suction tube.

In removing tissue according to the invention, the hand-held tool is turned on, as is a source of suction, so that the bur is caused to rotate within the suction tube, near the entrance end. Then, the tool is manipulated so that the sharpened edge of the suction tube scrapes the tissue in a manner to cause it to be removed from a larger tissue mass, and entrained or drawn into the suction tube. The rotating bur then grinds the tissue into much smaller bits so that such bits can be carried away by the suction to a remote containment vessel. The sharpened edge of the suction tube can be manipulated, much like a curette, to scrape both hard and soft tissue areas to remove deposits as well as tissue.

The removal of tissue according to the invention is greatly facilitated in that substantial time is saved, the tissue removing procedure becomes less tedious, the patient trauma and post-operative complications are reduced. Also, the tissue removing instrument of the invention is well adapted for removing that tissue which is desired to be removed, without damaging surrounding or adjacent tissue. With such procedure, any blood or fluid is also carried away to clear the area of concern.

BRIEF DESCRIPTION OF THE DRAWINGS

Further features and advantages will become apparent from the following and more particular description of the preferred and other embodiments of the invention, as illustrated in the accompanying drawings in which like reference characters generally refer to the same parts or elements throughout the views, and in which.

DETAILED DESCRIPTION OF THE INVENTION

Figure 1:
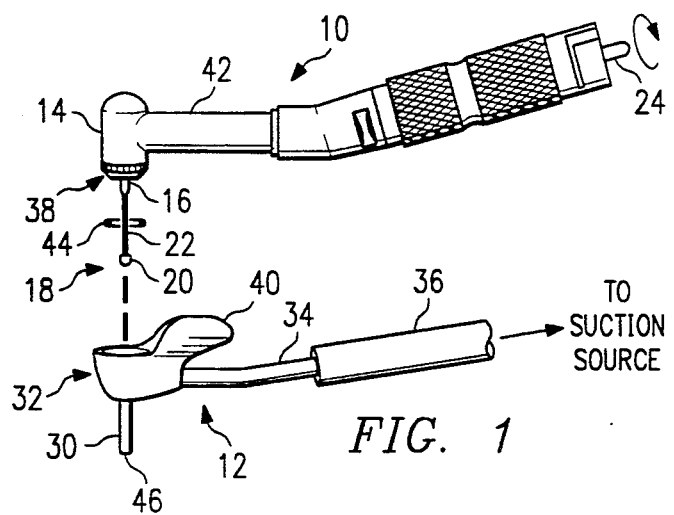
FIG. 1 is a side plan view of the tissue removing instrument of the invention, with some of the parts thereof removed for clarity.

FIG. 1 illustrates the principles and concepts of a tissue removing instrument well-adapted for use according to the invention. Shown is a power-driven hand tool 10 to which a suction tube assembly 12 is removably mounted. While the power-driven tool 10 is shown as a hand-held device, such tool may be of many other forms, including a robotic manipulated tool.

The power-driven tool 10 is of conventional construction, including a head 14 which houses a friction-type chuck (not shown) for holding the shank 16 of a bur 18. The bur 18 includes a grinding head 20 connected to the shank 16 by a shaft 22.

The power-driven tool 10 includes a rotatable shaft 24 which is driven by other electrical or air equipment (not shown). The shaft 24 is routed through the tool 10 by various bearings and gears so that the chuck in the head 14 is rotated, thereby also rotating the bur 18. The bur 18 is mounted within the chuck by simply pressing the shank 16 therein until bottomed so that the bur 18 is frictionally held within the chuck. Removal of the bur 18 is accomplished by forcefully pulling the bur 18 out of the chuck, or by pushing it out with a small shafted object, inserted via a small hole in the top of the head 14. Other types of chucks can be utilized with equal effectiveness.

The suction tube assembly 12 includes a hollow tube 30 molded integral with a plastic saddle member 32. A discharge tube 34 is also molded integral with the saddle member 32, and joined to the suction tube 30 internal to the saddle member 32 to form a continuous suction passage. The discharge tube 34 can be connected by a rubber hose 36 to a source of suction, via an intermediate containment vessel (not shown) for holding an accumulation of tissue removed according to the invention.

The saddle member 32 is molded so that it closely conforms to the shape of the bottom 38 of the tool head 14. In addition, the saddle member 32 includes a support portion 40 having curved wings which partially envelope and cradle the bottom cylindrical portion 42 of the power-driven tool 10. As can be appreciated, the saddle member 32 is molded to conform to the shape of the head 14 of the power-driven tool 10 so that when mounted thereto, the grinding head 20 of the bur 18 is radially centered within the tissue removing suction tube 30. The saddle member 32 is clamped or otherwise held to the power-driven tool 10 by wrapping a rubber band around the cylindrical tool part 42 and the saddle member 32. It is contemplated that the suction tube assembly 12 and the bur 18 will be employed for a single patient, and then disposed of thereafter. While the suction tube member assembly 32 is shown removably mounted to the power-driven tool 10, such is not a requirement, as a suction tube assembly could be made or formed integral with the power-driven tool 10. Indeed, those skilled in the art having this disclosure can employ the principles and concepts hereof to adapt readily available power-driven medical or dental instruments to accommodate the suction tube assembly as an integral unit therewith.

An elastomeric O-ring 44, shown in a removed location, functions to seal the lower portion 38 of the tool head 14 to the saddle member 32 to thereby prevent loss of suction therebetween. The suction available at the rubber hose 36 is thereby channeled to an entrance end 46 of the tissue removing suction tube 30. As will be described in more detail below, the entrance end 46 is preferably sharpened to facilitate removal of tissue from a larger tissue mass.

Figure 2:
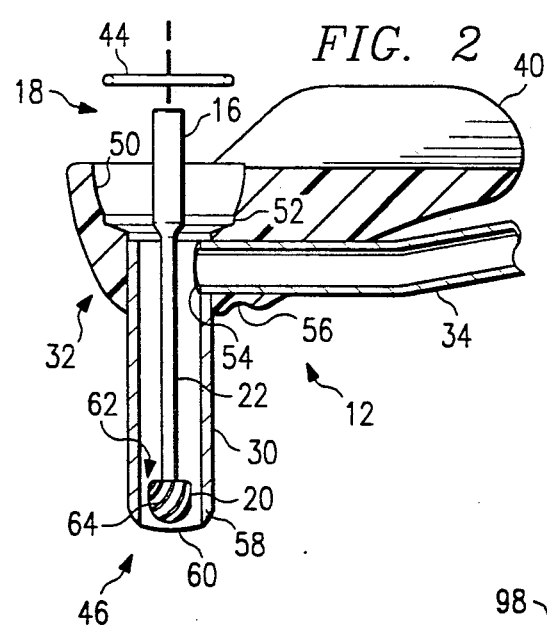
FIG. 2 is a partial cross-sectional view of the suction tube assembly.

Having described the general construction of the tissue removing instrument of the invention, reference is made to FIG. 2 where further details of the suction tube assembly 12 are shown. FIG. 2 illustrates a much enlarged cross-sectional view of the saddle member 32, while the bur 18 is not shown in cross section. In one embodiment of the invention, the suction tube assembly 12 includes a saddle member 32 formed of acrylic plastic, or other moldable material. The saddle member 32 is formed so that it conforms closely to the shape of the head 14 of the power-driven tool 10 so that the bur 18 is held in a registered position within the tissue removing suction tube 30. To that end, the saddle member 32 includes a cavity 50 having a shape which closely conforms to the lower portion 38 of the tool head 14. Also, a slight annular groove 52 is formed in the cavity 50 for holding the elastomeric O-ring 44.

The tissue removing suction tube 30 is constructed of surgical steel and molded within the plastic material of the saddle member 32 so that it is registered with respect to the cavity 50, thereby aligning the suction tube 30 with respect to the chuck held within the tool head 14. As further shown in FIG. 2, the saddle member 32 includes a portion 40 which cradles the cylindrical part 42 of the power-driven tool 10. The saddle member portion 40 cradles the cylindrical tool part 42 with an arc to the extent of about a 60°-180°. The saddle member cradle thereby prevents relative angular movement of the suction tube assembly 32 about an axis through the bur 18.

The plastic saddle member 32 also holds the tissue removing suction tube 30 with respect to the discharge tube 34. Preferably, a cutout 54 is formed in an upper portion of the tissue removing suction tube 30, and the end of the discharge tube 34 is welded thereto to form a suction passage between both such tubes. Preferably, the tissue removing suction tube 30 is constructed of a stainless steel or other surgical metal, while the discharge tube 34 may be of any kind of tubular stock which can be connected with respect to the tube 30. The saddle member 32 may include on a bottom section thereof, an indention 56 to accommodate a restraining member, such as a rubber band (not shown), for fastening the suction tube assembly 12 to the power-driven tool 10.

As further illustrated in FIG. 2, the tissue removing suction tube 30 includes an entrance end 46 for receiving tissue strands or pieces which are wholly or partially removed from another tissue mass. As clearly shown, the bur head 20 is recessed about 1.5 mm from the entrance end so that the grinding action of the bur head 20 does not damage tissue, except that which is entrained into the entrance end 46 of the tube 30. The recessed bur head 20 prevents damage to tissue which is not desired to be removed, even though it might be located adjacent to granulation tissue. The entrance end 46 of the tube 30 is preferably sharpened to facilitate the separation and/or removal of tissue pieces from a tissue mass. The entrance end 46 of the tissue removing suction tube 30 is shown having an outside bevel 58 which terminates at a sharp edge. Further, the entrance end 46 has an annular edge shape which is irregular. The irregular edge is defined by a pair of opposing lobes, one shown as reference character 60, which facilitate the scraping and separation of tissue so that the tissue can enter the suction tube 30 and be ground into smaller bits by the bur head 20. It is believed that the irregular shaped annular edge is not absolutely essential, although it appears to facilitate tissue removal.

In the preferred embodiment of the invention, the bur 18 is fabricated of stainless steel, or other surgical type of material. The bur 18 includes a cutting head 20 which is spaced apart a small distance from the internal sidewalls of the tissue removing suction tube 30 to thereby define a narrowed annular channel 62. The annular channel 62 defines an orifice which functions as a venturi so that the movement of air, occasioned by the suction, is accelerated. This venturi action facilitates the entraining of tissue within the entrance end 46 of the tissue removing suction tube 30, as well as carries tissue bits to the discharge tube 34 to minimize clogging. The bur head 20 includes spiral grinding teeth 64 which grind or mill the tissue drawn or forced into the entrance end 46 of the suction tube 30. The spacing between the bur head 20 and the internal sidewalls of the suction tube 30 is about 0.15 mm. With such clearance, the tissue is ground into very small bits, and drawn upwardly in the suction tube 30, out of the discharge tube 34 and into a remote collection container. In the preferred embodiment of the invention, the tissue removing suction tube 30 is similar to a conventional hypodermic needle, cut to a length of about 10 mm, and an internal diameter of about 1.5 mm. The use of a No. 6 bur head 20 provides an annular clearance in the suction tube 30 of the type noted.

Other configurations of grinding teeth are believed to be as effective in grinding tissue. For example, a grinding head having drill bit type of sharp spiral edges is well adapted for grinding tissue into small bits.

In addition, and according to another feature of the invention, the shank 16 of the bur 18 is milled to achieve an intermediate shaft 22 of a smaller diameter. In this manner, a larger annular space is provided in the suction tube 30 for conducting tissue bits, via the suction, and out of the discharge tube 34.

In operation, the tissue removing instrument of the invention is operated in the following manner. The bur 18 is first frictionally fastened within the chuck of the head 14 of the power-driven tool 10. The suction tube assembly 12 is then mounted or clipped to the tool 10, such that the bur 18 is aligned within the tissue removing suction tube 30, near the entrance end 46 thereof. The source of suction is then activated, as is the rotary power to the tool 10. Preferably, the bur 18 is rotated at a speed of about 5,000-10,000 rpm to achieve an efficient grinding of tissue. Different speeds and bur head configurations may be suitable for different types of tissues. A source of vacuum or suction, such as normally available in the medical or dental environment, is adequate. The instrument is then manipulated, manually or by other means, so that the entrance end 46 of the tissue removing suction tube 30 digs into or scrapes the tissue to be removed. The constant scraping of the tissue mass with the sharp entrance end 46 forces tissue into the grinding head 20 where it is pulverized or ground into small bits and conducted by the suction upwardly in the tube 30 and then out of the discharge tube 34. It can be appreciated that tissue bits no larger than annular orifice size 62 can be processed through the instrument. Because of the dual sharpened lobes 60 at the entrance end 46 of the tissue removing suction tube 30, the operator can move the tube in an arcuate motion in one direction to scrape tissue with one lobe 60, and back in the other direction to also scrape additional tissue with the opposing lobe. The ability to grind and quickly remove the tissue greatly reduces the time for overall tissue movement. In addition, the method of the invention is much improved over the prior technique, which was extremely tedious and fatiguing, giving rise to patient trauma. Importantly, a single instrument is effective to both remove tissue as well as suction body fluids. Periodically, after manipulation of the tissue removing instrument of the invention, it is inserted, while operating, into sterile saline solution to purge or clear the suction tube 30, as well as the grinding head 20. The suction draws water up into the tissue removing suction tube 30 to form a column of water in which the grinding head 20 is rotated, thereby cleaning the spiral cutting grooves 64.

Figure 3:
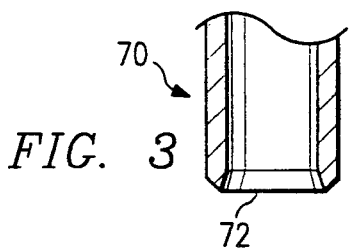
FIG. 3 is a cross-sectional view of one configuration of the entrance end of the suction tube.

With reference now to FIG. 3, there is shown a portion of a tissue removing suction tube 70. In this embodiment, the annular edge 72 of the entrance end is not irregular shaped, and is ground or sharpened in a bi-bevel manner, similar to a knife edge. Such an edge remains sharp over an extended period of usage to thereby protract the utility of the invention.

Figure 4:
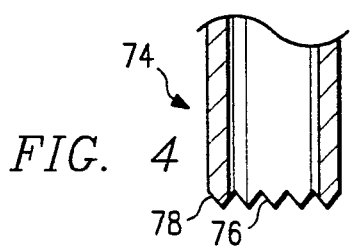
FIG. 4 is a cross-sectional view of another configuration of the entrance end of the suction tube.

FIG. 4 illustrates another embodiment of a tissue removing suction tube 74 having an annular edge, cut with teeth 76 therearound. The configuration of this embodiment is sharpened by forming an outside bevel 78, much like that described in conjunction with FIG. 2.

Figure 5:
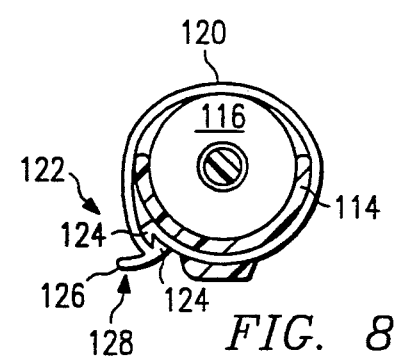
FIG. 5 illustrates another embodiment of a cutting bur adapted for use with the invention.

FIG. 5 illustrates a cutting head 80 which can be employed in lieu of the grinding head 20, shown in FIG. 2. The cutting head 80 includes a number of arms 82 each having a cutting edge 84. The arms 82 are sharpened on a leading edge to cut tissue when the cutter 80 is rotated in the direction shown by reference numeral 86. The cutters are sharpened on an upper edge thereof so that when the tissue is cut, the pieces are forced or directed upwardly, for removal by the suction. The cutter 80 is formed integral with a shaft 88 which is connected to a shank (not shown) for holding by the chuck of a power-driven tool.

With regard to other variations of grinding wheels, the bur shown in FIG. 2 can be bent very slightly so that the grinding head 20 traverses an annular path without contacting the internal sidewall of the suction tube 30. With this type of bur, tissue can be ground into very small bits.

Figure 6:
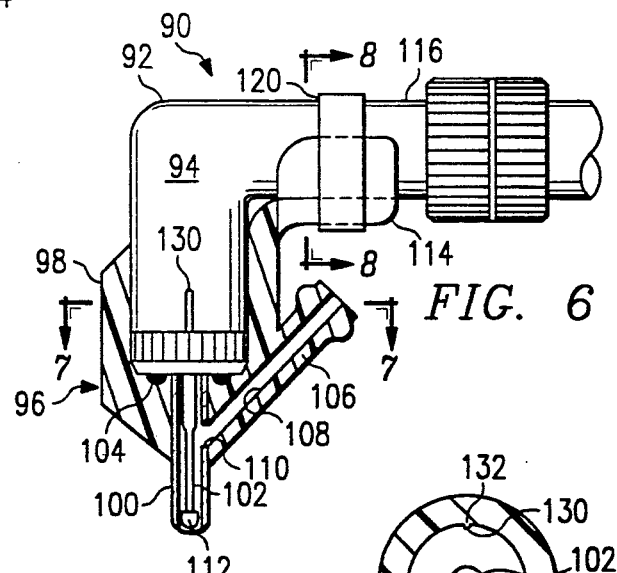
FIG. 6 is a partial cross-sectional view of another embodiment of the invention, including a saddle member for attaching a suction hood assembly to a hand-held power-driven tool.

FIG. 6 depicts a tissue removing instrument 90 constructed in accordance with another embodiment of the invention. The tissue removing instrument 90 includes a power-driven tool 92 of conventional design, typically employed by dentists. The power-driven tool 92 includes a head 94 having an internal chuck of the type described above. Removably attached to the head 94 of the power-driven tool 92 is a suction hood assembly 96 adapted for removable mounting to the power-driven tool 92. The suction hood assembly 96 includes a generally cylindrical section 98 which fits snugly around the cylindrical power tool head 94. Molded integral with the suction hood assembly 96 is a suction tube 100 for receiving therein the rotating bur 102. A suction tight fit is accomplished between the suction hood assembly 96 and the planar face of the power tool head 94 by an elastomeric O-ring 104. An annular channel is formed in the cavity of the suction hood assembly 96 for receiving a portion of the O-ring 104. A suction fitting 106 has formed therein a passage 108 for connecting the suction from a flexible rubber suction tube (not shown) to the internal portion of the suction tube 100. A hole 110 is formed in the sidewall of the suction tube 100 for completing the passage between the passageway 108 and the internal part of the suction tube 100. In this manner, when a suction is applied to the fitting 106, tissue ground into bits by the rotating bur head 112 is drawing upwardly in the tube 100, and out through the passageway 108 to a remote collection unit.

Also formed integral with the suction hood assembly 96 is a semi-cylindrical saddle member 114. The saddle member is shown in cross section in FIG. 8. The saddle member 114 preferably cradles the cylindrical body 116 of the power-driven tool 92, but can be formed with various shapes to accommodate the power-driven tool to be held thereto. The saddle member 114 is adapted to hold the suction hood 96 firmly to the power tool head 94 so that the O-ring 104 maintains a seal between the internal cavity of the suction hood 96 and the planar face of the power tool head 94. Preferably, the suction hood assembly 96 is molded of a plastic suitable for bonding to the metallic suction tube 100, as well as of the type which is low cost and easily formed by conventional plastic molding processes.

Figures 7, 8:
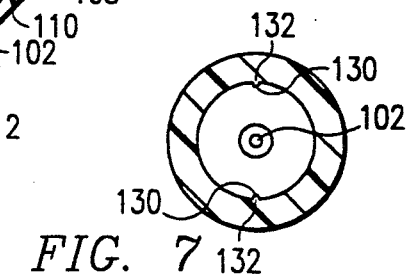
FIG. 7 is a cross-sectional view of the tissue removing instrument, taken along line 7—7 of FIG. 6.
FIG. 8 is a cross-sectional view, taken along line 8—8 of FIG. 6, showing the clamp for holding the suction hood assembly to the power-driven tool.

The saddle member 114 is held or clamped to the neck 116 of the power-driven tool 92 by a clamp 120. The clamp 120 is preferably of the type which can quickly and easily clamp the parts together, as well as be conveniently loosened and removed. The clamp believed to be readily adapted for use with the present invention is shown in FIG. 8. The clamp 120 is essentially a flexible plastic strip which can wrap entirely around the saddle member 114 and the neck 116 of the power-driven tool 92. Further, the clamp 120 includes interlocking ends 122. More specifically, both ends include interlocking teeth-like edges which, when locked together, firmly hold the saddle member 114 clamped against the power-driven tool neck 116. The interlocking teeth are shown as reference numerals 124. Other types of interlocking structures can be utilized with equal effectiveness. One end of the clamp 120 includes a short handle 126 which facilitates the unlocking of the teeth 124 and the removal of the clamp 120. By pressing the handle 126 in the direction indicated by reference number 128 the teeth become disengaged.

While the clamp 120 is shown as being constructed as a separate element, it can also be formed as two strips integral with the respective upper opposing edges of the saddle member 114. In addition, a standard tie wrap plastic strip can be utilized as a clamp for holding the saddle member 114 to the power-driven tool 92. Tie wraps are well known in the art for clamping bundles of wires together as a harness. A tie wrap presents certain advantages, in that it is adjustable to accommodate the circumference of different types of power-driven tools, and can become locked at any such circumference, and then released. Again, tie wrap elements can be constructed integral with the saddle member 114.

As yet another alternative, the saddle member 114 can be constructed in an arcuate shape of about 270 degrees, and then snap fit onto the neck 116 of the power-driven tool 92. The snap fit structure in many instances can eliminate the need for additional straps or clamps.

In accordance with another feature of the invention, the power-driven tool 92 has formed on the head 94 thereof one or more slots 130. The internal cavity of the suction hood assembly 96 has formed therein a corresponding number of ribs 132 which fit into the respective slots 130 and thereby prevent rotational movement of the hood 96 with respect to the head 94 of the power-driven tool 92.

As with the embodiment described above in connection with FIG. 2, the suction hood assembly 96 and related components are disposable after use on a patient. By fabricating a suction tube 100 having a sharpened end in the manner described above, and molding such tube integral with a plastic suction hood 96, the device can be economically constructed, and thus made for disposable use.

The suction tube assembly 32 and the suction hood assembly 96 can be fabricated using acrylic plastic, or other plastic readily adapted for molding. Those skilled in the plastic molding art construct molds for forming the plastic assemblies having shapes conforming to the respective power-driven tools. Such molds can be constructed to hold the suction tubes 30 or 100 so that the plastic can be molded therearound, and adhered to the metal suction tube.

From the foregoing, disclosed is a tissue removing instrument which is easily adapted to conventional dental or medical equipment. A technical advantage of the tissue removing instrument of the invention is that tissue can be more quickly removed than conventional curette devices. Another technical advantage in employing the tissue removing instrument of the invention is that the tissue can be more easily and cleanly removed, even in tight places, thereby reducing fatigue and the tedious nature of the operation. Yet another advantage of the invention is that it can be removably mounted to a standard rotational dental or medical tool. Yet another technical advantage of the invention is that the tissue removing instrument, and especially the saddle assembly thereof, can be economically constructed so as to provide a low cost disposable structure. An important technical advantage of the invention is that it substantially reduces aerosol contamination of tissue bits in the area of concern.

While the preferred and other embodiments of the invention have been disclosed with reference to specific tissue removing instruments, and methods of use thereof, it is to be understood that many changes in detail may be made as a matter of engineering choices, without departing from the spirit and scope of the invention, as defined by the appended claims.

What is claimed is:

1. An instrument for removing tissue, comprising:
   a tubular member structured for connection to a source of suction such that a suction is drawn through said tubular member, said tubular member having an open end defined by an edge sharpened around the circumference thereof for curetting a piece of tissue from a larger tissue mass;

a bur for rotation in said tubular member, said bur being adapted for grinding tissue piece entrained into said tubular member, said ground tissue being carried away and discharged by said suction; and a tool adapted for rotating said bur and adapted for attachment to said tubular member.

2. The tissue removing instrument of claim 1, wherein said bur includes a grinding head closely spaced between an internal circular sidewall of said tubular member to define an orifice.

3. The tissue removing instrument of claim 2, wherein said grinding head includes a shank of dimensions smaller than the bur head to facilitate removal of ground tissue and to reduce clogging.

4. The tissue removing instrument of claim 2, wherein said grinding head is closely spaced from said sidewall to form a venturi action.

5. The tissue removing instrument of claim 1, wherein said entrance end has an edge with an irregular, annular shape.

6. The tissue removing instrument of claim 1, wherein said tool comprises a contra-angle housing, and further including a saddle member formed integral with said tubular member, said saddle member being adapted for removable mounting to said contra-angle tool, and said saddle member having an internal shape complementary with an external portion of said tool for cradling the tool to provide registration therebetween, and a nonthreadable clamp for clamping the cradled tool to the saddle member.

7. The tissue removing instrument of claim 6, wherein said saddle member is snap-fittable to said tool.

8. The tissue removing instrument of claim 6, further including a suction passage connected to an internal portion of said tubular member.

9. The tissue removing instrument of claim 1, wherein said bur includes a grinding head that is circumferentially enclosed by said tubular member and recessed from a tissue entrance end of said tubular member so that said bur does not contact tissue that is not removed by the annular sharpened edge of the tubular member.

10. The tissue removing instrument of claim 1, wherein said tubular member is cut at an angle generally perpendicular to a longitudinal axis thereof to define said open end.

11. An instrument adapted for use with a power-driven tool for removing tissue, comprising:

a unitary disposable suction tube assembly structured for removable attachment to said power-driven tool, said suction tube assembly including, a) a plastic base molded to cradle a complementary shaped portion of said power-driven tool, the cradle engagement between the base and the power-driven tool providing registration therebetween, b) a clamp for clamping the plastic base to the power-driven tool to maintain said cradle engagement, said clamp being adapted for quick release of the plastic base from the power-driven tool, c) a suction tube having one end adapted for removing tissue, and another end molded in said plastic base, d) a discharge tube connected with respect to said suction tube for defining a passage for carrying tissue bits, said discharge tube being adapted for connection to a source of suction; and a bur connectable to the power-driven tool for rotation, said bur being disposed in said suction tube to grind tissue into small bits, and said cradle engagement between said plastic base and said power-driven tool providing registration of said bur within said suction tube.

12. The tissue removing instrument of claim 11, wherein said suction tube assembly is snap fittable to said power-driven tool.

13. The tissue removing instrument of claim 11, wherein said bur includes a grinding head recessed from an entrance end of said suction tube.

14. The tissue removing instrument of claim 11, wherein said suction tube includes an entrance end having a sharpened edge for curetting tissue and removing tissue strands from a tissue mass.

15. The tissue removing instrument of claim 14 wherein the entrance end of said suction tube includes an irregular shaped annular edge to facilitate tissue removal.

16. The tissue removing instrument of claim 11, wherein said suction tube assembly is generally butted against the power-driven tool and sealed thereto by an O-ring.

17. The tissue removing instrument of claim 11, wherein said suction tube assembly defines a hood having a cylindrical part fittable over an end of the power-driven tool, and includes a saddle member for clamping the suction tube assembly to a neck portion of the power-driven tool.

18. The tissue removing instrument of claim 17, further including a rib formed on an internal surface of the suction tube assembly cylindrical part, and a slot formed in a head portion of the power-driven tool, the rib and slot being engagable to prevent angular rotation of the suction tube assembly on the power-driven tool head.

19. The tissue removing instrument of claim 11, further including a saddle member formed integral with the suction tube assembly, and a fastening strap for clamping the saddle member and thus the suction tube assembly to the power-driven tool.

20. The tissue removing instrument of claim 11, wherein said discharge tube is molded from plastic with said base.

21. A method for removing tissue, comprising the steps of:

curetting fragments of granulation tissue from a tissue mass using a sharpened end of a hollow tube;

rotating a grinding head in the hollow tube to entrain the tissue fragments and to grind the tissue fragments into smaller bits; and utilizing a suction in the tube to remove the ground tissue fragments from the tube.

22. The method of claim 21, further including simultaneously grinding the tissue fragments into bits and employing the suction in the tube to remove the ground tissue bits.

23. The method of claim 21, further including suctioning body fluids through the tube to clear tissue areas for visual inspection.

24. The method of claim 21, further including employing a small diameter tube having a sharpened end for removing granulation tissue in periodontal operations.

25. The method of claim 21, further including mounting a suction tube assembly comprising said tube and a mount to a power driven tool, and connecting a source of suction to the assembly.

26. The method of claim 25, further including mounting the assembly in a sealing relationship to a head portion of the power-driven tool.

27. The method of claim 21, further including clamping a suction tube assembly comprising a plastic base with an embedded tube, with a quick release clamp, to a power-driven tool for rotating the bur within the tube.

28. An instrument adapted for attachment to a tool having a rotating shaft, and adapted for removing granulation tissue, comprising:
   a bur driven by the rotating shaft;
   a tubular member having a sharpened circular end edge, said tubular member being attachable to the tool for receiving therein and enclosing said bur, said bur being recessed a small distance from the inner sidewalls of the tubular member, and being recessed a small distance from the sharpened circular end edge of the tubular member so that the bur does not protrude beyond the end of the tubular member but yet readily engages tissue curetted by the sharp circular edge, whereby when a tissue strand is formed from a tissue mass by the sharpened edge and entrained in the end of the tubular member, the bur is effective to grind the tissue bit into smaller pieces for removal by suction from the instrument.

29. The tissue removing instrument of claim 28 wherein the end edge of the tubular member is cut so as to be orthogonal to the axis of the tubular member.

* * * * *

UNITED STATES PATENT AND TRADEMARK OFFICE
CERTIFICATE OF CORRECTION

PATENT NO. : 5,122,153

DATED : June 16, 1992

INVENTOR(S) : Stephen K. Harrel

It is certified that error appears in the above-indentified patent and that said Letters Patent is hereby corrected as shown below:

Column 9, line 2, after "grinding", insert --the--.

Column 9, line 3, after "tissue", insert --piece--.

Signed and Sealed this

Ninth Day of November, 1993

Attest:

BRUCE LEHMAN

*Attesting Officer*    *Commissioner of Patents and Trademarks*